(12) United States Patent
Hashimoto et al.

(10) Patent No.: US 11,090,351 B2
(45) Date of Patent: Aug. 17, 2021

(54) WHITENING AGENT

(71) Applicants: KAO CORPORATION, Tokyo (JP); BOGOR AGRICULTURAL UNIVERSITY, Bogor (ID)

(72) Inventors: Hiroshi Hashimoto, Haga-gun (JP); Mitsuyuki Hotta, Haga-gun (JP); Maeko Iwamura, Haga-gun (JP); Latifah Kasim Darusman; Irmanida Batubara, Bogor (ID); Edy Djauhari; Rudi Heryanto, Bogor (ID); Tohru Mitsunaga, Gifu (JP)

(73) Assignees: KAO CORPORATION, Tokyo (JP); BOGOR AGRICULTURAL UNIVERSITY, Bogor (ID)

(*) Notice: Subject to any disclaimer, the term of this patent is extended or adjusted under 35 U.S.C. 154(b) by 58 days.

(21) Appl. No.: 16/306,281

(22) PCT Filed: Feb. 17, 2017

(86) PCT No.: PCT/JP2017/006016
§ 371 (c)(1),
(2) Date: Nov. 30, 2018

(87) PCT Pub. No.: WO2017/145958
PCT Pub. Date: Aug. 31, 2017

(65) Prior Publication Data
US 2019/0167748 A1    Jun. 6, 2019

(30) Foreign Application Priority Data
Feb. 24, 2016    (WO) .................. PCT/JP2016/000980

(51) Int. Cl.
| | |
|---|---|
| A61K 36/61 | (2006.01) |
| A61Q 19/02 | (2006.01) |
| A61K 8/34 | (2006.01) |
| A61K 8/97 | (2017.01) |
| A61K 31/12 | (2006.01) |
| A61K 8/9789 | (2017.01) |
| A61K 8/35 | (2006.01) |

(52) U.S. Cl.
CPC .............. *A61K 36/61* (2013.01); *A61K 8/345* (2013.01); *A61K 8/35* (2013.01); *A61K 8/97* (2013.01); *A61K 8/9789* (2017.08); *A61K 31/12* (2013.01); *A61Q 19/02* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 5,872,254 A | 2/1999 | Kim et al. | |
| 6,214,352 B1 | 4/2001 | Matsukawa | |
| 6,514,538 B1 | 2/2003 | Ota et al. | |
| 6,521,267 B1 | 2/2003 | Steck | |
| 9,801,809 B2 | 10/2017 | Rana et al. | |

(Continued)

FOREIGN PATENT DOCUMENTS

| | | |
|---|---|---|
| DE | 10 2011 102 824 A1 | 12/2012 |
| JP | 05-155735 | 6/1993 |
| JP | 5-155750 A | 6/1993 |

(Continued)

OTHER PUBLICATIONS

Saifudin et al. (Planta Med 2012; 78: 1378-1381).*
Ismail et al. (Evidence-Based Complementary and Alternative Medicine, vol. 2013, Article ID 716532, 16 pages, 2013).*
Har et al. (Int. J Med Arom Plants, 2(2): 219-228, 2012).*
Su et al. (Int. J. Mol. Sci. 2013, 14, 20443-20458).*
English translation of KR20130052379 (2013).*
Esmaeili, et al., "Identification, determination, and study of antioxidative activities of hesperetin and gallic acid in hydro-alcoholic extract from flowers of *Eriobotrya japonica* (Lindl.)", Avicenna Journal of Phytomedicine (AJP), vol. 4, No. 4, Jul.-Aug. 2014, pp. 260-266.

(Continued)

*Primary Examiner* — Bong-Sook Baek
(74) *Attorney, Agent, or Firm* — Oblon, McClelland, Maier & Neustadt, L.L.P.

(57) ABSTRACT

Provision of a material, which has tyrosinase-inhibiting activity and is effective for skin whitening. A tyrosinase inhibitor comprising *Syzygium polyanthum* or an extract therefrom as an active ingredient is provided. Also, a compound represented by any one of the following formulae (I) to (III) and a tyrosinase inhibitor comprising the compound as an active ingredient are provided.

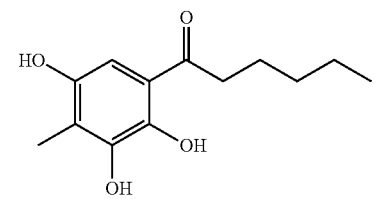

(I)

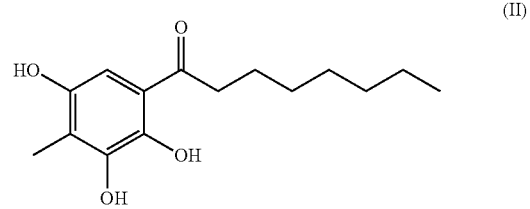

(II)

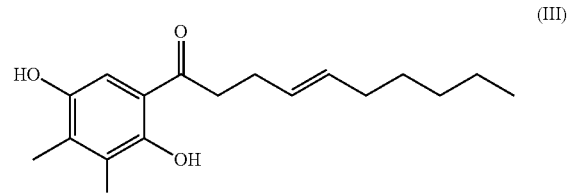

(III)

3 Claims, 1 Drawing Sheet

(56) References Cited

U.S. PATENT DOCUMENTS 10,537,516 B2    1/2020    Zhang et al.

FOREIGN PATENT DOCUMENTS

| JP | 11-106311 A | 4/1999 |
| JP | 2001-2888098 | 10/2001 |
| JP | 2001-316239 | 11/2001 |
| JP | 2002-047130 | 2/2002 |
| JP | 2002-275026 | 9/2002 |
| JP | 2009-227612 | 10/2009 |
| KR | 10-2013-0052379 A | 5/2013 |
| KR | 20130052379 * | 5/2013 |
| WO | WO 2015/000064 A1 | 1/2015 |

OTHER PUBLICATIONS

Ercisli, et al., "Color and Antioxidant Characteristics of Some Fresh Fig (*Ficus carica* L.) Genotypes from Northeastrn Turkey", Plant Foods Hum. Nutr., vol. 67, 2012, pp. 271-276.

Liu, et al., "Effects of Chinese Herbal Extracts on Tyrosinase Activity and Melanogenesis", Natural Products Chemistry & Research, vol. 3, No. 4, 2015, pp. 1-5.

International Search Report dated Jan. 2, 2016 in PCT/JP2017/006016 filed Feb. 17, 2017, 5 pages.

Alvaro Sfinchez-Ferrer, et al., "Tyrosinase: a Comprehensive Review of its Mechanism" Biochimica et Biophysica Acta, 1247, 1995, pp. 1-11.

Irawan Wijaya Kusuma, et al., "Biological Activity and Phytochemical Analysis of Three Indonesian Medicinal Plants, Murraya Koenigii, Syzygium Polyanthum and Zingiber Purpurea" Journal of Acupuncture and Meridian Studies, vol. 4, No. 1, XP055271190, Mar. 2011, pp. 75-79.

Enos Tangke Arung, et al., "Inhibitory Components from the Buds of Clove (*Syzygium aromaticum*) on Melanin Formation in B16 Melanoma Cells" Fitoterapia, vol. 82, No. 2, XP002757523, Mar. 2011, pp. 198-202.

Paula Monteiro Souza, et al., "Plants from Brazilian Cerrado with Potent Tyrosinase Inhibitory Activity" PLOS ONE, vol. 7, No. 11, XP055271519, Nov. 16, 2012, e48589, 7 pages.

Azis Saifudin, et al., "Protein Tyrosine Phosphatase 1B (PTP1B)-Inhibiting Constituents from the Leaves of Syzygium Polyanthum" Planta Medica, Thieme Verlag, DE, XP009194061, Feb. 1, 2013, pp. 1378-1381 and cover letter.

\* cited by examiner

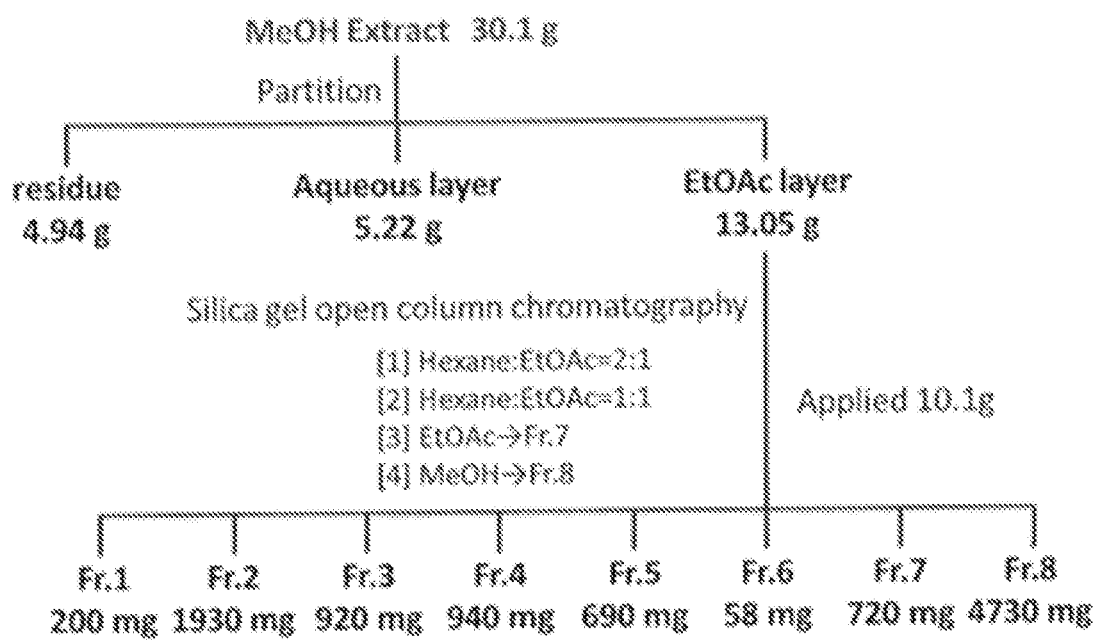
Separation scheme of *S. polyanthum* leaves MeOH extract

WHITENING AGENT

FIELD OF THE INVENTION

The present invention relates to a material effective for skin whitening.

BACKGROUND OF THE INVENTION

Pigmentation, spots, and freckles on skin are believed to occur generally as a result of enhanced melanogenesis by the activation of pigment cells (melanocytes) in skin by stimulation by exposure of skin to ultraviolet rays, hormonal abnormality, a genetic factor, or the like. The mechanism of the enhanced melanogenesis is complicated, but it is known that melanin is bio-synthesized by the action of the enzyme tyrosinase and that the DOPA oxidase activity of the tyrosinase is deeply involved in the mechanism of the melanogenesis (Non Patent Literature 1).

Whitening agents targeting the mechanism of melanogenesis have been developed. For example, ascorbic acid, arbutin, kojic acid, etc. (Non-Patent Literature 2) and a variety of plant extracts are reported as skin whitening agents which has a melanogenesis-suppressing action by suppressing the activity of the enzyme tyrosinase. Moreover, there are a large number of reports on the plant extracts which suppress the DOPA oxidase activity and have the whitening effect.

CITATION LIST (Non-Patent Document 1) Biochimica et Biophysica Acta, 1247, 1-11 (1995)

(Non-Patent Document 2) Advanced Cosmetic Dermatology, IV. Clinical pharmacology of skin whitening agent ("Bihaku senryaku, IV. Bihakuzaino yakuri to rinsho" in Japanese,) NANKODO Co., Ltd., p. 95-116

SUMMARY OF THE INVENTION

The present invention provides a tyrosinase inhibitor comprising *Syzygium polyanthum* or an extract therefrom as an active ingredient.

The present invention provides a melanogenesis inhibitor comprising *Syzygium polyanthum* or an extract therefrom as an active ingredient.

Moreover, the present invention provides a skin whitening agent comprising *Syzygium polyanthum* or an extract therefrom as an active ingredient.

Furthermore, the present invention provides a compound represented by any of the following formulae (I) to (III).

Furthermore, the present invention provides a tyrosinase inhibitor comprising, as an active ingredient, at least one selected from the group consisting of compounds represented by the following formulae (I) to (III).

Furthermore, the present invention provides a melanogenesis inhibitor comprising, as an active ingredient, at least one selected from the group consisting of compounds represented by the following formulae (I) to (III).

Furthermore, the present invention provides a skin whitening agent comprising, as an active ingredient, at least one selected from the group consisting of compounds represented by the following formulae (I) to (III).

Chem.1

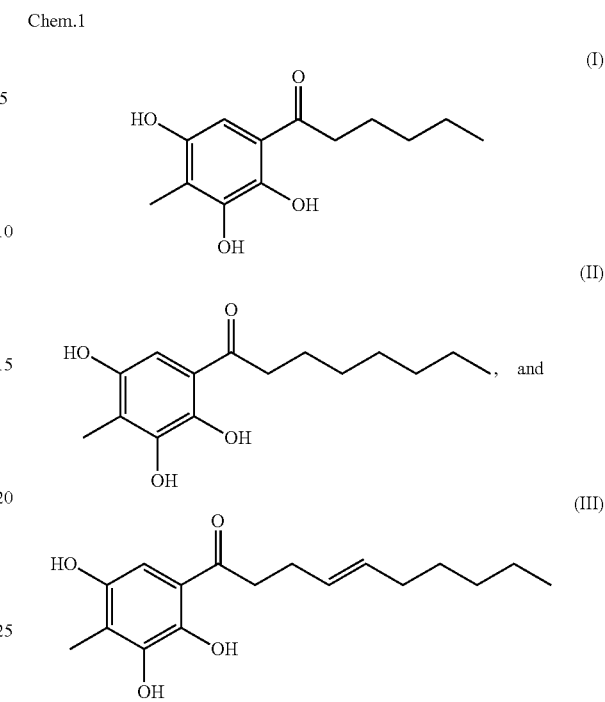

BRIEF DESCRIPTION OF THE DRAWING

The FIGURE illustrates the scheme of fractioning in Example 3.

DETAILED DESCRIPTION OF THE INVENTION

All patent documents, non-patent documents, and other publications cited in the present description are incorporated herein by reference in their entirety.

The present invention relates to providing a material effective for skin whitening having a tyrosinase-inhibiting activity and a melanogenesis-inhibiting activity.

As a result of extensive studies, the present inventors found a plant which inhibits a tyrosinase activity and suppresses melanogenesis in skin melanocytes. Moreover, the present inventors found new compounds having an activity of inhibiting a tyrosinase activity and suppressing melanogenesis in skin melanocytes from the plant.

The present invention provides plant-derived materials having a tyrosinase inhibitory activity and a melanogenesis inhibitory activity. These materials are effective for skin whitening.

The term "non-therapeutic" is used in the present description to include a concept, which does not include medical treatments, namely, a concept, which does not include a method for performing an operation on, treating or diagnosing a human, and more specifically, a concept, which does not include a method by which a doctor or a person who has received instructions from the doctor performs an operation on, treats, or diagnoses a human.

The term "prevention" as used in the present description means prevention, suppression or delay of the onset of symptom or condition in individual bodies, or reduction in the risk of the onset of symptom or condition in individual bodies. The term "amelioration" as used in the present description means an improvement in symptom or condition, prevention, suppression or delay of aggravation of symptom or condition, or reverse, prevention, suppression or delay of the progress of symptom or condition.

*Syzygium polyanthum* used in the present invention is a plant in the family Myrtaceae and also referred to as Salam in Indonesia. *Syzygium polyanthum* has been used conventionally for diarrhea, abdominal pain, diabetes, hangover, psoriasis, and an itch and its leaves are eaten as a colorant or a flavoring agent mixed in rise dishes. Meanwhile, *Syzygium polyanthum* has never been used for skin whitening.

In the present invention, any part of *Syzygium polyanthum*, for example, a whole tree, leaf (including leaf blade and leafstalk), bark, wood, branch, fruit, fruit skin, seed, flower (including petal and ovary), or root of the plant or a combination thereof can be used. Preferably, leaves are used as *Syzygium polyanthum*.

In the present invention, any of the above described parts of *Syzygium polyanthum* may be directly used, or may also be used after it has been cut, crushed, ground or exploited. Otherwise, a dry product thereof may also be used. Preferably, a dry product of the plant is used. Also, such a dry product may be cut, crushed, ground or powdered.

The extract of *Syzygium polyanthum* used in the present invention may be an extract obtained by directly extracting from any part of the above described parts of *Syzygium polyanthum*, or an extract obtained by extraction from the part of the plant which has been dried, cut, crushed, ground or exploited. Preferably, the extract is an extract from a dry product of leaves of *Syzygium polyanthum*, or an extract from the dry product, which has been cut, crushed, ground or powdered.

Examples of an extraction means for obtaining the extract, which can be used herein, include ordinary extraction means, such as solid-liquid extraction, squeezing extraction, liquid-liquid extraction, immersion, decoction, percolation, reflux extraction, Soxhlet extraction, ultrasonic extraction, microwave extraction, and stirring. These extraction means may be used in combination. For example, immersion or solid-liquid extraction may be combined with liquid-liquid extraction. In the case of reducing the extraction time, solid-liquid extraction involving stirring may be carried out.

The solvent used for extraction of the extract may be either a polar solvent or a nonpolar solvent, and these solvents may also be used in combination. Examples of the extraction solvent include: water; monohydric or polyhydric alcohols; ketones such as acetone or methyl ethyl ketone; esters such as methyl acetate or ethyl acetate; chain and cyclic ethers such as tetrahydrofuran or diethyl ether; polyethers such as polyethylene glycol; halogenated hydrocarbons such as dichloromethane, chloroform, or carbon tetrachloride; hydrocarbons such as hexane, cyclohexane, or petroleum ether; aromatic hydrocarbons such as benzene or toluene; pyridines; supercritical carbon dioxide; and fats and oils, waxes, and other oils. The above-listed solvents can be used singly or in combination of two or more solvents. An example of such a combination of solvents is a mixed solvent of monohydric alcohol or polyhydric alcohol and water.

Alternatively, the plant extract may also be prepared by repeated extraction using different solvents.

Examples of the monohydric alcohol include methanol, ethanol, propanol, butanol, amyl alcohol, hexanol, heptanol, and octanol. Examples of the polyhydric alcohol include: divalent alcohols such as ethylene glycol, propylene glycol, 1,3-butylene glycol, 1,4-butanediol, 1,5-pentanediol, or 1,6-hexanediol; and tri- or more hydric alcohols such as glycerin. Among these alcohols, monohydric or polyhydric alcohol having 1 to 4 carbon atoms is preferable, and from the viewpoint of versatility, monohydric alcohol and dihydric alcohol are preferable. More preferred examples include methanol, ethanol, 1,3-butylene glycol, n-propanol, isopropanol, n-butanol, isobutanol, sec-butanol, and t-butanol. Methanol and ethanol are further preferable.

Examples of a mixed solvent of monohydric alcohol or polyhydric alcohol and water include mixed solvents of the above-listed monohydric alcohols and water, and mixed solvents of the above-listed polyhydric alcohols and water. A preferred example is a mixed solvent of water and alcohol selected from the group consisting of methanol, ethanol, 1,3-butylene glycol, n-propanol, isopropanol, n-butanol, isobutanol, sec-butanol and t-butanol. A more preferred example is a mixed solvent of methanol or ethanol and water.

The concentration of alcohol in the mixed solvent of monohydric alcohol or polyhydric alcohol and water is preferably 10 volume % or more, more preferably 20 volume % or more, and further preferably 30 volume % or more and preferably 90 volume % or less, more preferably 80 volume % or less, and further preferably 70 volume % or less. Otherwise, examples of the concentration of alcohol in the mixed solvent of water/alcohol include from 10 to 90 volume %, from 10 to 80 volume %, from 10 to 70 volume %, from 20 to 90 volume %, from 20 to 80 volume %, from 20 to 70 volume %, from 30 to 90 volume %, from 30 to 80 volume % and from 30 to 70 volume %.

In a preferred embodiment, the solvent used in extraction of the plant extract is selected from water, monohydric alcohol, polyhydric alcohol and a mixed solvent of monohydric alcohol or polyhydric alcohol and water, more preferably water, methanol, ethanol or a mixed solvent of methanol or ethanol and water, and further preferably water, methanol or a mixed solvent of ethanol and water.

Examples of the concentration of methanol or ethanol in the mixed solvent of methanol or ethanol and water include from 10 to 90 volume %, from 1 to 80 volume %, from 10 to 70 volume %, from 20 to 90 volume %, from 20 to 80 volume %, from 20 to 70 volume %, from 30 to 90 volume %, from 30 to 80 volume % and from 30 to 70 volume %, more preferably from 40 to 60 volume % and further preferably 50 volume %.

The amount of the solvent used in extraction is preferably from 1 to 100 mL with respect to 1 g of the plant (in terms of dry mass). Extraction conditions are not particularly limited, as long as extraction is sufficiently carried out under the conditions. In general, if the solvent is at a lower temperature, extraction is carried out for a longer period of time, and if the solvent is at a higher temperature, extraction is carried out for a shorter period of time. For example, the extraction time is preferably 1 hour or more, and more preferably 4 hours or more. On the other hand, it is preferably 2 months or less, and more preferably 4 weeks or less. Moreover, for example, the extraction temperature is preferably 0° C. or higher, and more preferably 5° C. or higher. Also, it is preferably a solvent boiling point or lower, and more preferably approximately from 10° C. to 80° C., and it may also be approximately a room temperature. Examples of preferred extraction conditions include a temperature of from 15° C. to 40° C. for from 3 days to 4 weeks, and from 50° C. to 70° C. for from 1 to 10 hours. However, extraction conditions are not limited thereto, and can be selected, as appropriate, by a person skilled in the art.

A purification treatment, which is commonly used in the production of a plant extract, can be performed, as necessary, on the extract obtained by the aforementioned procedures. Examples of such a purification treatment include organic solvent precipitation, centrifugation, ultrafiltration membrane, high performance liquid chromatography, column chromatography, liquid-liquid distribution, gel filtration separation, and a treatment of using activated carbon or the like.

With regard to the extract obtained by the aforementioned procedures, the extract solution or a fraction thereof may be directly used singly or in combination, or it may be diluted with a suitable solvent and it may be then used in the form of a diluted solution. Otherwise, the extract may be processed into a concentrated extract, dry powder, or a paste, and it may be then used.

As will be described in Examples later, the extract of *Syzygium polyanthum* has tyrosinase inhibitory activity and melanogenesis inhibitory activity in the skin melanocyte and suppresses melanogenesis in the skin (see. Examples 1-2). Accordingly *Syzygium polyanthum* or an extract therefrom can be used as an active ingredient for inhibiting tyrosinase and for inhibiting melanogenesis. Otherwise, *Syzygium polyanthum* or the extract therefrom can be used as an active ingredient for suppressing melanogenesis in the skin and for whitening skin.

According to the present invention, *Syzygium polyanthum* and extracts therefrom may be used singly, or may also be used in combination of any two or more. In a preferred embodiment, an extract from *Syzygium polyanthum* is used.

Furthermore, the present inventors found novel compounds represented by the following formulae (I) to (III) as an active ingredient of *Syzygium polyanthum*.

Chem.2

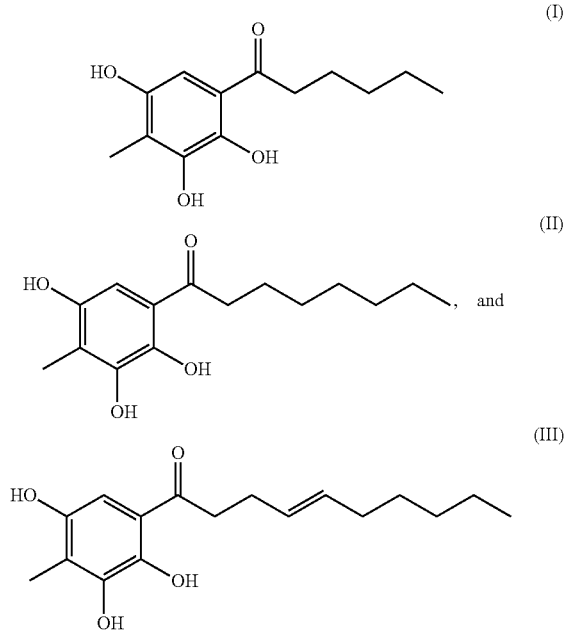

The compounds represented by the formulae (I) to (III) can be used as an active ingredient for inhibiting tyrosinase inhibition and for inhibiting melanogenesis. Furthermore, these compounds can be used as an active ingredient for suppressing melanogenesis in the skin and for whitening skin. In the present invention, the compounds represented by the formulae (I) to (III) may be used singly, or may also be used in combination of two or three. Furthermore, according to the present invention, any one, two or three of the compounds represented by the formulae (I) to (III) may be used in combination with *Syzygium polyanthum* and/or an extract therefrom.

Preferably, the extract of *Syzygium polyanthum* used in the present invention contains an extract from the leaves of *Syzygium polyanthum*.

Accordingly, in one aspect, the present invention provides a tyrosinase inhibitor comprising *Syzygium polyanthum* or an extract therefrom as an active ingredient. Moreover, the present invention provides a melanogenesis inhibitor comprising *Syzygium polyanthum* or an extract therefrom as an active ingredient. Furthermore, the present invention provides a skin whitening agent comprising *Syzygium polyanthum* or an extract therefrom as an active ingredient.

In another aspect, the present invention provides use of *Syzygium polyanthum* or an extract therefrom for production of a tyrosinase inhibitor, a melanogenesis inhibitor or a skin whitening agent.

In one embodiment, the agent can be essentially composed of *Syzygium polyanthum* or an extract therefrom.

In another aspect, the present invention provides a tyrosinase inhibitor comprising, as an active ingredient, at least one selected from the group consisting of compounds represented by the following formulae (I) to (III). Moreover, the present invention provides a melanogenesis inhibitor comprising, as an active ingredient, at least one selected from the group consisting of compounds represented by the following formulae (I) to (III). Furthermore, the present invention provides a skin whitening agent comprising, as an active ingredient, at least one selected from the group consisting of compounds represented by the following formulae (I) to (III).

In another embodiment, the present invention provides use of at least one selected from the group consisting of compounds represented by the following formulae (I) to (III) for production of a tyrosinase inhibitor, a melanogenesis inhibitor or a skin whitening agent.

In one embodiment, the agent is essentially composed of at least one selected from the group consisting of compounds represented by the following formulae (I) to (III).

In one embodiment, the tyrosinase inhibitor, melanogenesis inhibitor or skin whitening agent can comprise one or more selected from the group consisting of *Syzygium polyanthum*, extracts therefrom and compounds represented by the formulae (I) to (III) as an active ingredient.

In another aspect, the present invention provides use of *Syzygium polyanthum* or an extract therefrom for inhibiting tyrosinase, inhibiting melanogenesis or skin whitening.

In a further another aspect, the present invention provides *Syzygium polyanthum* or an extract therefrom for use in inhibiting tyrosinase, inhibiting melanogenesis or skin whitening.

In another aspect, the present invention provides use of at least one selected from the group consisting of compounds represented by the following formulae (I) to (III) for inhibiting tyrosinase, inhibiting melanogenesis or skin whitening.

In further another aspect, the invention provides at least one selected from the group consisting of compounds represented by the following formulae (I) to (III) for use in inhibiting tyrosinase, inhibiting melanogenesis or skin whitening.

In one embodiment, one or more selected from the group consisting of *Syzygium polyanthum*, extracts therefrom and compounds represented by the formulae (I) to (III) can be used for the tyrosinase inhibition, melanogenesis inhibition or skin whitening.

The use according to the present invention may be either therapeutic use or non-therapeutic use. Examples of the therapeutic use include use for a patient affected with a disease caused by overproduction of melanin (e.g., chloasma, acquired dermal melanocytosis, etc.). Examples of the non-therapeutic use include use for inhibition of skin melanogenesis or skin whitening for cosmetic purposes. Moreover, other examples of the non-therapeutic use include the provision of one or more selected from the group consisting of *Syzygium polyanthum*, extracts therefrom and compounds represented by the formulae (I) to (III) to another person for the administration or ingestion thereof, not as a medical treatment, but for obtaining the effect of inhibiting skin melanogenesis or whitening skin.

In the present invention, *Syzygium polyanthum*, an extract therefrom and compounds represented by the formulae (I) to (III) can be used for both a human and a non-human animal. Examples of such a non-human animal include non-human mammals and birds. Examples of such a non-human mammal include an anthropoid (ape), other primates, a mouse, a rat, a hamster, a horse, a bovine, a swine, a sheep, a goat, a dog, a cat, and a companion animal.

In the present invention, *Syzygium polyanthum*, an extract therefrom and compounds represented by the formulae (I) to (III) can be used as an active ingredient for imparting a function of tyrosinase inhibition, melanogenesis inhibition or skin whitening to pharmaceutical products, quasi drugs, cosmetics, food products or the like.

The pharmaceutical product (including quasi drug) is for inhibiting tyrosinase or inhibiting melanogenesis, and comprises at least one selected from the group consisting of *Syzygium polyanthum*, extracts therefrom and compounds represented by the formulae (I) to (III) as an active ingredient for exhibiting the function. Furthermore, the pharmaceutical product may also comprise pharmaceutically acceptable carriers, other active ingredients, pharmacological components, and the like, as necessary, unless the function of the active ingredient is lost.

The mode of administration of the pharmaceutical product (including quasi drug) may be either of oral administration and parenteral administration. The dosage form of the pharmaceutical product is not particularly limited, as long as it is a dosage form suitable for oral or parenteral administration. Examples of such a dosage form include an injection, a suppository, an inhalant, a transdermal absorption agent, various types of external agents, a topical formulation, a tablet, a capsule, a granule, a powder agent, a liquid agent, and syrup. These formulations having various dosage forms can be prepared by appropriately combining one or more selected from the group consisting of *Syzygium polyanthum*, extracts therefrom and compounds represented by the formulae (I) to (III) with a pharmaceutically acceptable carrier (e.g., an excipient, a binder, a filler, a thickener, a disintegrator, a surfactant, a lubricant, a dispersant, a buffer, a preservative, a corrigent, a flavor, a coating agent, a diluent, etc.), other medicinal components and the like according to an ordinary method.

The content of *Syzygium polyanthum* or an extract therefrom (in terms of dry mass) in the pharmaceutical product (including quasi drug) is not particularly limited. It is preferably 0.01% by mass or more, more preferably 0.1% by mass or more, even more preferably 1.0% by mass or more, further preferably 10% by mass or more, and even further preferably 15% by mass or more, based on the total mass, and it is preferably 95% by mass or less, more preferably 80% by mass or less, and even more preferably 60% by mass or less, based on the total mass. Moreover, examples of the content include from 0.01 to 95% by mass, from 0.01 to 80% by mass, from 0.01 to 60% by mass, from 0.1 to 95% by mass, from 0.1 to 80% by mass %, from 0.1 to 60% by mass, from 1.0 to 95% by mass, from 1.0 to 80% by mass, from 1.0 to 60% by mass, from 10 to 95% by mass, from 10 to 80% by mass, from 10 to 60% by mass, from 15 to 95% by mass, from 15 to 80% by mass, and from 15 to 60% by mass.

The total content of the compounds represented by the formulae (I) to (III) in the pharmaceutical product (including quasi drug) is not particularly limited. It is preferably 0.01% by mass or more, more preferably 0.1% by mass or more, even more preferably 1.0% by mass or more, further preferably 10% by mass or more, and even further preferably 15% by mass or more, based on the total mass, and it is preferably 95% by mass or less, more preferably 80% by mass or less, and even more preferably 60% by mass or less, based on the total mass. Moreover, examples of the content include from 0.01 to 95% by mass, from 0.01 to 80% by mass, from 0.01 to 60% by mass, from 0.1 to 95% by mass, from 0.1 to 80% by mass %, from 0.1 to 60% by mass, from 1.0 to 95% by mass, from 1.0 to 80% by mass, from 1.0 to 60% by mass, from 10 to 95% by mass, from 10 to 80% by mass, from 10 to 60% by mass, from 15 to 95% by mass, from 15 to 80% by mass, and from 15 to 60% by mass.

The cosmetics are cosmetics for inhibiting tyrosinase, inhibiting melanogenesis or skin whitening and comprise one or more selected from the group consisting of *Syzygium polyanthum*, extracts therefrom and compounds represented by the formulae (I) to (III) as an active ingredient for the function. Furthermore, the cosmetic may also comprise a carrier acceptable for cosmetics, or other active ingredients or cosmetic components, such as a moisturizer, other whitening agents, a UV protectant, a cell activator, a cleaning agent, a keratolytic agent, a makeup component (e.g., makeup base, foundation, face powder, powder, cheek color, lipstick, eye makeup, eyebrow, mascara, and others), and the like, as necessary, unless the function of the active ingredient is lost. Examples of the form of the cosmetic include cosmetic forms for external administration to the skin, local administration, and oral administration.

The cosmetic can be produced by combining one or more selected from the group consisting of *Syzygium polyanthum*, extracts therefrom and compounds represented by the formulae (I) to (III) with the above described carrier acceptable for cosmetics, or other active ingredients or cosmetic components, and the like, as necessary, according to an ordinary method.

The content of *Syzygium polyanthum* or an extract therefrom (in terms of dry mass) in the cosmetic is not particularly limited. It is preferably 0.0001% by mass or more, more preferably 0.001% by mass or more, even more preferably 0.01% by mass or more, further preferably 0.1% by mass or more, and even further preferably 1.0% by mass or more, based on the total mass and, it is preferably 60% by mass or less, more preferably 40% by mass or less, even more preferably 20% by mass or less, and even further preferably 10% by mass or less, based on the total mass. Moreover, examples of the content include from 0.0001 to 60% by mass, from 0.0001 to 40% by mass, from 0.0001 to 20% by mass, from 0.0001 to 10% by mass, from 0.001 to 60% by mass, from 0.001 to 40% by mass, from 0.001 to 20% by mass, from 0.001 to 10% by mass, from 0.01 to 60% by mass, from 0.01 to 40% by mass, from 0.01 to 20% by mass, from 0.01 to 10% by mass, from 0.1 to 60% by mass, from 0.1 to 40% by mass, from 0.1 to 20% by mass, from 0.1 to 10% by mass, from 1.0 to 60% by mass, from 1.0 to 40% by mass, from 1.0 to 20% by mass, and from 1.0 to 10% by mass.

The total content of the compounds represented by the formulae (I) to (III) in the cosmetic is not particularly limited. It is preferably 0.0001% by mass or more, more preferably 0.001% by mass or more, even more preferably 0.01% by mass or more, further preferably 0.1% by mass or more, and even further preferably 1.0% by mass or more, based on the total mass and, it is preferably 60% by mass or less, more preferably 40% by mass or less, even more preferably 20% by mass or less, and even further preferably 10% by mass or less, based on the total mass. Moreover, examples of the content include from 0.0001 to 60% by mass, from 0.0001 to 40% by mass, from 0.0001 to 20% by mass, from 0.0001 to 10% by mass, from 0.001 to 60% by mass, from 0.001 to 40% by mass, from 0.001 to 20% by mass, from 0.001 to 10% by mass, from 0.01 to 60% by mass, from 0.01 to 40% by mass, from 0.01 to 20% by mass, from 0.01 to 10% by mass, from 0.1 to 60% by mass, from 0.1 to 40% by mass, from 0.1 to 20% by mass, from 0.1 to 10% by mass, from 1.0 to 60% by mass, from 1.0 to 40% by mass, from 1.0 to 20% by mass, and from 1.0 to 10% by mass.

The food product is a food product for providing a function of tyrosinase inhibition, melanogenesis inhibition or skin whitening and comprises one or more selected from the group consisting of *Syzygium polyanthum*, extracts therefrom and compounds represented by the formulae (I) to (III) as an active ingredient for the function. The food product includes food products for sick persons and food products with health claims, such as food products with nutrient function claims, food products for specified health uses, or food products with a labeling system on food functions, the concept of each of which is tyrosinase inhibition, melanogenesis inhibition or skin whitening and which are attended with a labeling system on the concept, as necessary.

The form of the food product may be a solid, semi-solid, or liquid (e.g., beverages). Examples of the food product include breads, needles, rice products, confectioneries such as cookies, jellies, dairy products, soup products, frozen food products, convenience food products, processed starch products, processed fish meat products, other processed food products, condiments, supplements, beverages such as tea or coffee beverages, fruit drinks, carbonated drinks or jelly-like drinks, and the raw materials thereof. Alternatively, the food product may also be a supplement having the form of an oral administration preparation, such as a tablet, a capsule, a granule, powder, a liquid agent, or syrup.

The food product can be produced by appropriately combining one or more selected from the group consisting of *Syzygium polyanthum*, extracts therefrom and compounds represented by the formulae (I) to (III) with any given food product materials or additives acceptably used for food products (e.g., a solvent, a softener, oil, an emulsifier, an antiseptic, a flavor, a sweetener, a stabilizer, a coloring agent, an ultraviolet absorber, an antioxidant, a moisturizer, a thickener, a fixing agent, a dispersant, a wetting agent, etc.) according to an ordinary method.

The content of *Syzygium polyanthum* or an extract therefrom (in terms of dry mass) in the food product is not particularly limited. It is preferably 0.0001% by mass or more, more preferably 0.001% by mass or more, even more preferably 0.01% by mass or more, based on the total mass and, it is preferably 50% by mass or less, more preferably 20% by mass or less, even more preferably 10% by mass or less, based on the total mass. Moreover, examples of the content include from 0.0001 to 50% by mass, from 0.0001 to 20% by mass, from 0.0001 to 10% by mass, from 0.001 to 50% by mass, from 0.001 to 20% by mass, from 0.001 to 10% by mass, from 0.01 to 50% by mass, from 0.01 to 20% by mass, and from 0.01 to 10% by mass.

The total content of the compounds represented by the formulae (I) to (III) in the food product is not particularly limited. It is preferably 0.0001% by mass or more, more preferably 0.001% by mass or more, even more preferably 0.01% by mass or more, based on the total mass and, it is preferably 50% by mass or less, more preferably 20% by mass or less, even more preferably 10% by mass or less, based on the total mass. Moreover, examples of the content include from 0.0001 to 50% by mass, from 0.0001 to 20% by mass, from 0.0001 to 10% by mass, from 0.001 to 50% by mass, from 0.001 to 20% by mass, from 0.001 to 10% by mass, from 0.01 to 50% by mass, from 0.01 to 20% by mass, and from 0.01 to 10% by mass.

In another aspect, the present invention provides a method for inhibiting a tyrosinase in a subject. Moreover, the present invention provides a method for inhibiting melanogenesis in a subject. Moreover, the present invention provides a method for whitening skin in a subject. These methods comprise administering to a subject an effective amount of one or more selected from the group consisting of *Syzygium polyanthum*, extracts therefrom and compounds represented by the formulae (I) to (III). These methods may be either therapeutic methods or non-therapeutic methods.

The subject in the methods is an animal, for which tyrosinase inhibition, melanogenesis inhibition, or skin whitening is desired, or which needs it. Examples of such an animal include the aforementioned human and non-human animals, and the animal is more preferably a human. Otherwise, examples of the subject in the methods include sites on the skin, for which whitening is desired, or which need it (e.g., sites on the skin having pigmentation, spots, senile pigment freckles, etc. and light-exposure sites on the skin).

The present invention further provides a method for inhibiting in vitro tyrosinase or melanogenesis. This in vitro method can be carried out on the aforementioned human or non-human animal-derived tissues or cells, for example, skin tissues, 3D cultured skin or skin cells such as cultured keratinocytes, or an extract solution therefrom, or a reaction solution comprising tyrosinase and tyrosine or L-DOPA as a substrate thereof.

The effective dose amount to be administered in the methods according to the present invention can be an amount, in which tyrosinase activity in a subject or melanogenesis can be suppressed. The effective amount is preferably an amount, in which the activity of tyrosinase in an administration group can be statistically significantly reduced in compared to that in a non-administration group. Also, the effective amount is preferably an amount, in which the amount of melanin in skin cells in an administration group such as skin tissue-derived cells, 3D cultured skin, or cultured melanocytes can be statistically significantly reduced in compared to that in a non-administration group. Also, the effective amount is preferably an amount, in which the activity of tyrosinase in an administration group can be reduced to 50% or less, more preferably 70% or less of that in a non-administration group. Also, the effective amount is preferably an amount, in which the amount of melanin in an administration group can be reduced to 50% or less, more preferably 70% or less of that in a non-administration group. The tyrosinase activity can be determined by measuring the change of color of the reaction solution due to the reaction product of tyrosinase and its substrate based on absorbance. The amount of melanin can be determined by measuring the color strength of the solution containing melanin extracted from skin cells based on absorbance. However, the assays described above are examples and procedures for measuring the tyrosinase activity and the amount of melanin in cells are well-known to those skilled in the art.

The applied dose and dosage regimen of *Syzygium polyanthum*, extracts therefrom and compounds represented by the formulae (I) to (III) may be appropriately determined by a person skilled in the art depending on the species, body weight, sex, age or conditions of a subject, or other factors in the present invention. The applied dose of *Syzygium polyanthum* or an extract therefrom (in terms of dry mass), for example, per adult per day is preferably 0.0001 mg or more, more preferably 0.001 mg or more, even more preferably 0.01 mg or more, further preferably 0.1 mg or more, even further preferably 1 mg or more, still further preferably 0.1 g or more, and still further preferably 1 g or more, and it is also preferably 10 g or less, more preferably 5 g or less, and even more preferably 1 g or less, but the dose is not limited thereto. Otherwise, the applied dose (per adult per day) of *Syzygium polyanthum* or an extract therefrom according to the present invention (in terms of dry mass) can be selected from the range of, for example, from 0.0001 mg to 10 g, from 0.0001 mg to 5 g, from 0.0001 mg to 1 g, from 0.001 mg to 10 g, from 0.001 mg to 5 g, from 0.001 mg to 1 g, from 0.01 mg to 10 g, from 0.01 mg to 5 g, from 0.01 mg to 1 g, from 0.1 mg to 10 g, from 0.1 mg to 5 g, from 0.1 mg to 1 g, from 1 mg to 10 g, from 1 mg to 5 g, from 1 mg to 1 g, from 0.1 g to 10 g, from 0.1 g to 5 g, from 0.1 g to 1 g, from 1 g to 10 g, or from 1 g to 5 g. It is preferable to divide the above described amount, for example, once a day, or two or three times or more a day, and to continuously administer it to a subject for several weeks to several months.

The total applied dose of the compounds represented by the formulae (I) to (III) according to the present invention per adult per day is preferably 0.0001 mg or more, more preferably 0.001 mg or more, even more preferably 0.01 mg or more, further preferably 0.1 mg or more, even further preferably 1 mg or more, still further preferably 0.1 g or more, and still further preferably 1 g or more, and it is also preferably 10 g or less, more preferably 5 g or less, and even more preferably 1 g or less, but the dose is not limited thereto. Otherwise, the applied dose (per adult per day) of the compounds represented by the formulae (I) to (III) can be selected from the range of, for example, from 0.0001 mg to 10 g, from 0.0001 mg to 5 g, from 0.0001 mg to 1 g, from 0.001 mg to 10 g, from 0.001 mg to 5 g, from 0.001 mg to 1 g, from 0.01 mg to 10 g, from 0.01 mg to 5 g, from 0.01 mg to 1 g, from 0.1 mg to 10 g, from 0.1 mg to 5 g, from 0.1 mg to 1 g, from 1 mg to 10 g, from 1 mg to 5 g, from 1 mg to 1 g, from 0.1 g to 10 g, from 0.1 g to 5 g, from 0.1 g to 1 g, from 1 g to 10 g, or from 1 g to 5 g. It is preferable to divide the above described amount, for example, once a day, or two or three times or more a day, and to continuously administer it to a subject for several weeks to several months.

Also, the present invention includes, as illustrative embodiments, the following substances, production methods, intended uses, methods, and the like. However, the present invention is not limited to these embodiments.

<1> A tyrosinase inhibitor comprising *Syzygium polyanthum* or an extract therefrom as an active ingredient.

<2> A melanogenesis inhibitor comprising *Syzygium polyanthum* or an extract therefrom as an active ingredient.

<3> A skin whitening agent comprising *Syzygium polyanthum* or an extract therefrom as an active ingredient.

<4> Use of *Syzygium polyanthum* or an extract therefrom for production of a tyrosinase inhibitor.

<5> Use of *Syzygium polyanthum* or an extract therefrom for production of a melanogenesis inhibitor.

<6> Use of *Syzygium polyanthum* or an extract therefrom for production of a skin whitening agent.

<7> *Syzygium polyanthum* or an extract therefrom for use in inhibiting tyrosinase.

<8> *Syzygium polyanthum* or an extract therefrom for use in inhibiting melanogenesis.

<9> *Syzygium polyanthum* or an extract therefrom for use in skin whitening.

<10> Use of *Syzygium polyanthum* or an extract therefrom for inhibiting tyrosinase.

<11> Use of *Syzygium polyanthum* or an extract therefrom for inhibiting melanogenesis.

<12> Use of *Syzygium polyanthum* or an extract therefrom for whitening skin.

<13> A method for inhibiting a tyrosinase in a subject, comprising administering to the subject an effective amount of *Syzygium polyanthum* or an extract therefrom.

<14> A method for inhibiting melanogenesis in a subject, comprising administering to the subject an effective amount of *Syzygium polyanthum* or an extract therefrom.

<15> A method for whitening skin in a subject, comprising administering to the subject an effective amount of *Syzygium polyanthum* or an extract therefrom.

<16> In any one of the above <10> to <12>, the use is preferably non-therapeutic use.

<17> In any one of the above <1> to <16>, the extract is preferably an extract with of water, methanol, ethanol or a mixed solvent methanol or ethanol and water and more preferably an extract with methanol or a mixed solvent ethanol and water.

<18> In the above <17>, the mixed solvent of methanol or ethanol and water is preferably a 30-70 volume % ethanol aqueous solution or a 30-70 volume % methanol aqueous solution.

<19> In any one of the above <1> to <18>, the *Syzygium polyanthum* is preferably a leaf of *Syzygium polyanthum*.

<20> A compound represented by any of the formulae (I) to (III) below (but not in a form contained in *Syzygium polyanthum* or an extract therefrom).

<21> A composition comprising a compound represented by any of the formulae (I) to (III) below and one or more selected from the group consisting of pharmaceutically-acceptable carriers, carriers acceptable for cosmetics, additives acceptable for cosmetic ingredients and food products (provided that the compound represented by any of the formulae (I) to (III) is not in a form contained in *Syzygium polyanthum* or an extract therefrom).

<22> A tyrosinase inhibitor comprising, as an active ingredient, at least one compound selected from the group consisting of compounds represented by the following formulae (I) to (III).

<23> A melanogenesis inhibitor comprising, as an active ingredient, at least one compound selected from the group consisting of compounds represented by the following formulae (I) to (III).

<24> A skin whitening agent comprising, as an active ingredient, at least one compound selected from the group consisting of compounds represented by the following formulae (I) to (III).

<25> Use of at least one selected from the group consisting of compounds represented by the following formulae (I) to (III) for production of a tyrosinase inhibitor.

<26> Use of at least one selected from the group consisting of compounds represented by the following formulae (I) to (III) for production of a melanogenesis inhibitor.

<27> Use of at least one selected from the group consisting of compounds represented by the following formulae (I) to (III) for production of a skin whitening agent.

<28> At least one selected from the group consisting of compounds represented by the following formulae (I) to (III) for use in inhibiting tyrosinase.

<29> At least one selected from the group consisting of compounds represented by the following formulae (I) to (III) for use in inhibiting melanogenesis.

<30> At least one selected from the group consisting of compounds represented by the following formulae (I) to (III) for use in skin whitening.

<31> Use of at least one selected from the group consisting of compounds represented by the following formulae (I) to (III) for inhibiting tyrosinase.

<32> Use of at least one selected from the group consisting of compounds represented by the following formulae (I) to (III) for inhibiting melanogenesis.

<33> Use of at least one selected from the group consisting of compounds represented by the following formulae (I) to (III) for whitening skin.

<34> A method for inhibiting a tyrosinase in a subject, comprising administering to the subject an effective amount of at least one selected from the group consisting of compounds represented by the following formulae (I) to (III).

<35> A method for inhibiting melanogenesis in a subject, comprising administering to the subject an effective amount of at least one selected from the group consisting of compounds represented by the following formulae (I) to (III).

<36> A method for whitening skin in a subject, comprising administering to the subject an effective amount of at least one selected from the group consisting of compounds represented by the following formulae (I) to (III).

Chem.3

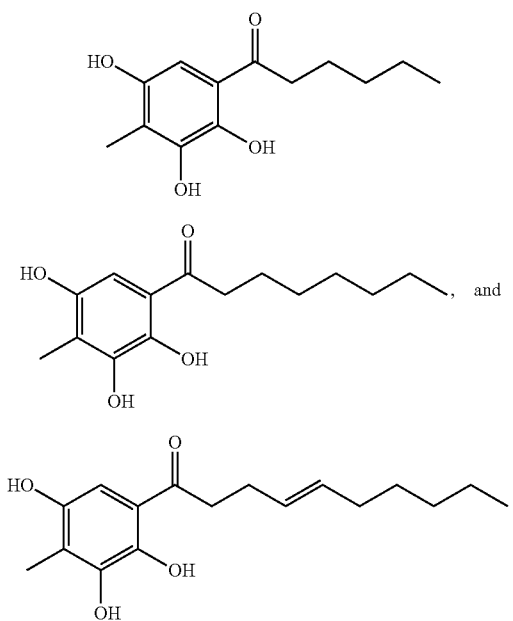

<37> In the any one of above <1> to <19>, the extract of *Syzygium polyanthum* comprises preferably an extract from the leaves of *Syzygium polyanthum*.

<38> A skin whitening product comprising *Syzygium polyanthum* or extract thereof as an active ingredient at a concentration minimum of 0.01% by mass and maximum of 95% by mass.

<39> The skin whitening product according to <38>, wherein the product has the activity of inhibiting tyrosinase.

<40> The skin whitening product according to <38>, wherein the product has the activity of inhibiting melanogenesis.

<41> The skin whitening product according to <38>, wherein the product consists of an extract of *Syzygium polyanthum* extracted using water and/or alcoholic solvents.

<42> The skin whitening product according to <41>, wherein the extract of water and or alcoholic solvent is derived from leaves.

<43> A skin whitening product comprising, as an active ingredient, at least one selected from the group consisting of compounds represented by the following formulae (I) to (III):

Chem.4

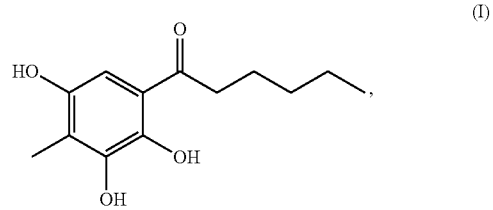

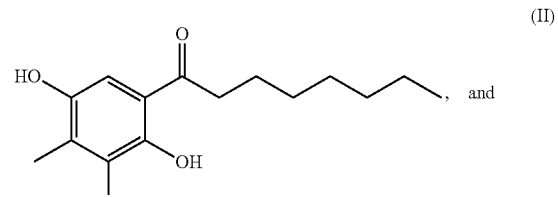

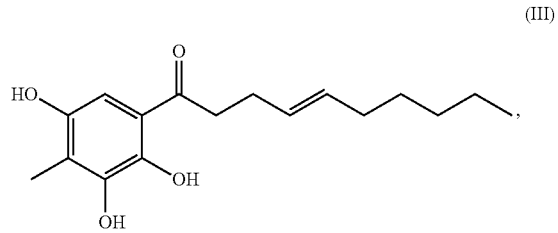

at a concentration minimum of 0.0001 mg and maximum of 10 g per adult per day

<44> The skin whitening product according to <43>, wherein the product has the activity of inhibiting tyrosinase.

<45> The skin whitening product according to <43>, wherein the product has the activity of inhibiting melanogenesis.

<46> The skin whitening product according to <43>, wherein the product consists of *Syzygium polyanthum* in extract form water and/or alcoholic solvents.

<47> The skin whitening product according to <46>, wherein the extract of water and or alcoholic solvent is derived from leaves.

EXAMPLES (Production Example 1) Preparation of Water Extract from *Syzygium polyanthum*

500 mL of water was added to 50 g of leaves of *Syzygium polyanthum* (manufactured by UD. Sari Alam, Tawangmangu, Karanganyar, Central Java, Indonesia), extraction was performed at 60° C. for 4 hours, and the resultant was filtered to obtain a crude extract solution. The crude extract solution was then concentrated and dried to obtain 10 g of an extract solid. This extract solid was dissolved in DMSO so that concentrations of the solid became 62.5-10000 ppm (w/v) and solutions of water extract of *Syzygium polyanthum* were prepared at different concentrations.

(Production Example 2) Preparation of 50% Ethanol Extract from *Syzygium polyanthum*

500 mL of 50% (v/v) ethanol was added to 50 g of leaves of *Syzygium polyanthum* (manufactured by UD. Sari Alam, Tawangmangu, Karanganyar, Central Java, Indonesia), extraction was performed at room temperature for 7 days, and the extract was filtered to obtain a crude extract solution. The crude extract solution was then concentrated and dried to obtain 10 g of an extract solid. This extract solid was dissolved in DMSO so that concentrations of the solid became 62.5-10000 ppm (w/v) and solutions of 50% ethanol extract of *Syzygium polyanthum* were prepared at different concentrations.

(Production Example 3) Preparation of Methanol Extract from *Syzygium polyanthum*

2.5 L of methanol was added to 500 g of leaves of *Syzygium polyanthum* (manufactured by UD. Sari Alam, Tawangmangu, Karanganyar, Central Java, Indonesia), extraction was performed at room temperature for 1 day, and the extract was filtered to obtain a crude extract solution. The crude extract solution was then concentrated and dried for 3 days to obtain 70 g of an extract solid.

Example 1 Tyrosinase Activity Assay

The tyrosinase activity assay was conducted to examine the tyrosinase-inhibiting activity of the extracts from *Syzygium polyanthum*.

(1) Tyrosinase-Inhibiting Activity of Water and 50% Ethanol Extracts from *Syzygium polyanthum*

70 µL of the extract solutions prepared in Production Examples 1-2 were transferred into a 96 well plate and 30 µL of the tyrosinase solution (a solution of 333 unit/mL mushroom tyrosinase (SIGMA) in 50 mM phosphate buffer, pH 6.5) and 110 µL of the substrate solution (2 mM L-tyrosine or 12 mM L-DOPA) were added. Kojic acid was used instead of extract as a positive control. The reaction solution was incubated at 37° C. for 30 minutes, absorbance at 492 nm was then measured using a microplate reader, and IC50 (the final concentration that exhibits 50% inhibition (in terms of dry mass)) was calculated.

(2) Tyrosinase Inhibiting Activity of Methanol Extract 1 mg of methanol extract from *Syzygium polyanthum* prepared in Production Example 3 was dissolved in 50 µL of DMSO and 550 µL of a buffer (50 mM solution of disodium hydrogen phosphate, pH 6.5). This extract solution was transferred in a 96 well plate so that the final concentrations of extract became 500, 250, 125, 62.5, 31.25, 15.625, 7.8125 and 0 µg/mL and diluted to 60 µL with the buffer. 30 µL of the tyrosinase solution (a buffered solution of 1 mg/16 mL mushroom tyrosinase (SIGMA), pH 6.5) and 110 µL of the substrate solution (2 mM L-tyrosine or 12 mM L-DOPA) were added to each well of the 96 well plate. Kojic acid was used instead of extract as a positive control. The reaction solution was allowed for reaction at 37° C. for 30 minutes, absorbance at 510 nm was then measured using a microplate reader, and IC50 was calculated.

The results of the tyrosinase activity assays are illustrated in Tables 1 and 2. The water extract, the 50% ethanol extract and the methanol extract from *Syzygium polyanthum* all inhibited tyrosinase activity.

TABLE 1

| Sample | Extraction solvent | IC50/ppm Tyrosine | DOPA |
|---|---|---|---|
| *Syzygium polyanthum* (Leaf) extract | Water | 156 | 305 |
| *Syzygium polyanthum* (Leaf) extract | 50% (v/v) EtOH | 73 | 95 |
| Kojic acid | — | 9 | 20 |

TABLE 2

| Sample | Extraction solvent | IC50/ppm Tyrosine | DOPA |
|---|---|---|---|
| *Syzygium polyanthum* (Leaf) extract | MeOH | 37 | 105 |
| Kojic acid | — | 6 | 27 |

Example 2 Inhibition of Melanogenesis in Skin Melanocytes (1) Culture of Skin Melanocytes B16 melanoma cells (DS pharma Biomedical) were used as skin melanocytes. The B16 melanoma cells were cultured in a $CO_2$ incubator (37° C., 5% $CO_2$) in 10 cm dishes containing the DMEM medium supplemented with 10% FBS. A cell suspension at $5.0 \times 10^4$ cells/mL was prepared from the cultured cells. 998 µL aliquots of the cell suspension were dispensed into 24 well plates and cultured in a $CO_2$ incubator (37° C., 5% $CO_2$) overnight. Subsequently, 2 µL of the DMSO solution of the methanol extract from *Syzygium polyanthum* prepared in Production Example 3 was added to each well (the final concentrations of the extract: 25 and 50 µg/mL) and the mixtures were further cultured for 72 hours. Arbutin (730 µM) was used instead of the extract as a positive control. DMSO was used as control.

(2) Calculation of Amount of Melanin

The supernatants of the cultures prepared in (1) were collected, 200 µL each was transferred into a 96 well plate, and then the absorbance was measured at 510 nm. The relative amount of extracellular melanin was calculated by determining the relative value to the control.

(3) Cytotoxicity Test (MTT Assay)

The MTT assay solution was prepared by dissolving 50 mg of Thiazolyl Blue Tetrazolium Bromide (SIGMA) in 10 mL of PBS (−). 50 µL of the MTT assay solution was added to each culture prepared in (1) and reacted for 4 hours. Then, 1 mL of isopropanol for MTT was added to each culture and the plate was covered with aluminum foil and allowed for reaction at room temperature for 2 hours for the reaction. After the reaction, the total amount was collected and centrifuged (1.45×10³ rpm, 1 min), then 150 µL each of the supernatants was transferred into a 96 well plate, and the absorbance was measured at 590 nm. The relative cell survival rate (cytotoxicity) was calculated by determining the relative value to the control.

The result of the relative amount of extracellular melanin and the relative cell survival rate of the melanocytes are illustrated in Table 3. The extract from *Syzygium polyanthum* decreased the amount of extracellular melanin in melanocytes in a concentration-dependent manner. Meanwhile, the cell survival rate of the melanocytes was high enough in the presence of high concentrations of the extract from *Syzygium polyanthum*.

TABLE 3

|  | *Syzygium polyanthum* extract (µg/mL) | | Arbutin |
|---|---|---|---|
|  | 25 | 50 | (730 µM) |
| Melanogenesis Activity (%) | 69.7 | 59.2 | 21.3 |
| Cell Viability (%) | 101 | 109 | 99 |

Example 3 Separation of Active Compound from *Syzygium polyanthum* Leaf

Leaves of *Syzygium polyanthum* were cut into small pieces, then dried under sunlight while covered with a black cloth and powdered. 500 g of powder was subjected to static extraction with 2.5 L of methanol for 24 hours. The extraction was repeated 3 times. The obtained extract was filtered, the solvent was removed with an evaporator, and the extract was dried naturally. To the obtained methanol extract was added an appropriate amount of distilled water and the mixture was stirred with a stirrer. An equal amount of ethyl acetate was then added and an ethyl acetate layer and an aqueous layer were obtained using a separatory funnel. The solvent was removed from the ethyl acetate layer with an evaporator, followed by drying. The extract was dissolved in ethyl acetate and applied to a glass column (80 mm diameter×520 mm length) filled with silica gel wet with n-hexane:ethyl acetate=2:1 (v/v). The elution was made with n-hexane:ethyl acetate=2:1 (v/v), 1:1(v/v), ethyl acetate, and methanol in this order to obtain 8 fractions (Fr. 1-8). The scheme of fractioning is illustrated in the FIGURE.

The tyrosinase activity assay of the obtained 8 fractions as samples was conducted in a procedure similar to that in Example 1 (3). Each fraction was dissolved in 600 µL of DMSO and added to 96-well plates to the final concentrations of 50, 25 and 12.5 µg/mL. The result is illustrated in Table 4. Strong activities were detected in Fr. 4-5.

TABLE 4

| IC50 (µg/mL) | Fr. 1 | Fr. 2 | Fr. 3 | Fr. 4 | Fr. 5 | Fr. 6 | Fr. 7 | Fr. 8 |
|---|---|---|---|---|---|---|---|---|
| Tyrosine | 229.83 | 276.76 | >500 | 7.12 | 37.26 | >500 | 356.62 | 268.23 |
| DOPA | >500 | 486.18 | >500 | 63.28 | 79.14 | >500 | >500 | >500 |

Furthermore, the 8 fractions were analyzed in HPLC. As a result, it was concluded that the isolation of compounds from Fr. 5 should be promising. Therefore, Fr. 5 was subjected to preparative HPLC. As a result, fractions exhibiting a single peak in HPLC analysis were isolated. These fractions were analyzed for structure by NMR and MALDI-TOF-MS analyses. As a result, Compounds 1-3 as illustrated below were found.

(Preparative HPLC Conditions)
Instrument: Jasco
Column: Inert Sustain C18.5 µm (4.6×250 mm)
Detector wavelength: 360 nm
Flow rate: 5.0 mL/min
Gradient Program: MeOH:0.05% TEAaq.=60%:40%→100%:0%
(NMR)
Instrument: JEOL ECA600NMR
Solvent: CD₃OD, C₃D₆O
Scan: ¹H-NMR 8, ¹³C-NMR 1000
(MALDI-TOF-MS)
Instrument: SIMADZU BIOTECH AXIMA RESONANCE
Ion mode: negative ion mode
Low: 100+
Power: 120

Chem.6

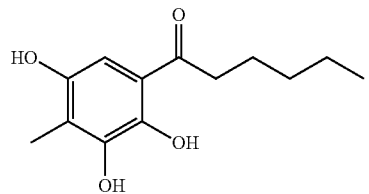

Compound 1

1-(2,3,5-Trihydroxy-4-methylphenyl)hexane-1-one

| Position | $\delta_H$ (ppm) | J(Hz) | $\delta_C$ (ppm) |
|---|---|---|---|
| 1 | | | 103.8 |
| 2 | | | 160.0 |
| 3 | | | 163.7 |
| 4 | | | 102.2 |
| 4-Me | 1.89 s | | 6.0 |
| 5 | | | 162.4 |
| 6 | 5.87 s | | 93.4 |
| 1' | | | 206.2 |
| 2' | 3.00 t | 7.6 | 43.6 |
| 3' | 1.63 quint | 7.4 | 24.8 |
| 4' | 1.33 m | | 31.6 |
| 5' | 1.33 m | | 22.3 |
| 6' | 0.90 t | 7.2 | 13.0 |

$\lambda_{max}$ 252, 292 nm; ¹H-NMR (METHANOL-D4, 600 MHz): δ ppm 5.87 (1H, s, H-6), 3.00 (2H, t, J=7.6 Hz, $H_2$-2'), 1.89 (3H, s, 4-$CH_3$), 1.63 (2H, quint, J=7.4 Hz, $H_2$-3'), 1.33 (4H-1, m, $H_2$-4", $H_2$-5"), 0.90 (3H, t, 0.1=7.2 Hz, $H_2$-6'); $^{13}$C-NMR (METHANOL-D4, 150 MHz): δppm 206.2 (C-1'), 163.7 (C-3), 162.4 (C-5), 160.0 (C-2), 103.8 (C-1), 102.2 (C-4), 93.4 (C-6), 43.6 (C-2'), 31.6 (C-4'), 24.8 (C-3'), 22.3 (C-5'), 13.0 (C-6'), 6.0 (4-$CH_3$)

MALDI-TOF-MS m/z 237.4 [M-H]$^-$

Chem. 7

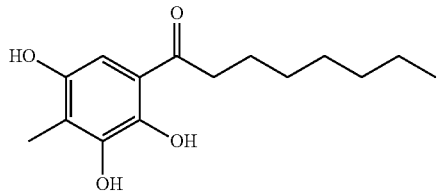

Compound 2

1-(2,3,5-Trihydroxy-4-methylphenyl)octane-1-one

| Position | $δ_H$ (ppm) | J(Hz) | $δ_C$ (ppm) |
|---|---|---|---|
| 1 | | | 103.8 |
| 2 | | | 160.0 |
| 3 | | | 163.6 |
| 4 | | | 102.2 |
| 4-Me | 1.89 s | | 6.0 |
| 5 | | | 162.4 |
| 6 | 5.87 s | | 93.5 |
| 1' | | | 206.3 |
| 2' | 3.00 t | 7.6 | 43.6 |
| 3' | 1.62 quint | 7.6 | 25.1 |
| 4' | 1.31 m | | 29.3 |
| 5' | 1.31 m | | 29.0 |
| 6' | 1.31 m | | 31.6 |
| 7' | 1.31 m | | 22.4 |
| 8' | 0.88 t | 7.2 | 13.1 |

$λ_{max}$ 252, 288 nm; $^1$H-NMR (METHANOL-D4, 600 MHz): δ ppm 5.87 (1H, s, 11-6), 3.00 (2H, t, J=7.6 Hz, $H_2$-2'), 1.89 (3H, s, 4-$CH_3$), 1.62 (2H, quint, J=7.6 Hz, $H_2$-3"), 1.31 (8H, m, $H_2$-4', $H_2$-5", $H_2$-6", $H_2$-7'), 0.88 (3H, t, J=7.2 Hz, $H_2$-8'); $^{13}$C-NMR (METHANOL-D4, 150 MHz): δ ppm 206.3 (C-1"), 163.6 (C-3), 162.4 (C-5), 160.0 (C-2), 103.8 (C-1), 102.2 (C-4), 93.5 (C-6), 43.6 (C-2"), 31.6 (C-6"), 31.6 (C-6'), 29.3 (C-4'), 29.0 (C-5"), 25.1 (C-3"), 22.4 (C-7"), 13.1 (C-3'), 6.0 (4-$CH_3$)

MALDI-TOF-MS m/z 265.4 [M-H]$^-$

Chem. 8

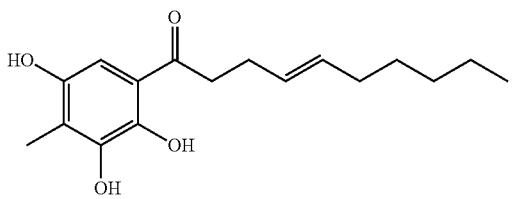

Compound 3

(4E)-1-(2,3,5-Trihydroxy-4-methylphenyl)dec-4-en-1-one

| Position | $δ_H$ (ppm) | J(Hz) | $δ_C$ (ppm) |
|---|---|---|---|
| 1 | | | 103.8 |
| 2 | | | 160.0 |
| 3 | | | 163.6 |
| 4 | | | 102.2 |
| 4-Me | 1.89 s | | 6.0 |
| 5 | | | 162.5 |
| 6 | 5.88 s | | 93.4 |
| 1' | | | 205.3 |
| 2' | 3.04 t | 7.2 | 43.6 |
| 3' | 2.37 q | 7.3 | 22.8 |
| 4' | 5.36 m | | 128.4 |
| 5' | 5.36 m | | 130.2 |
| 6' | 2.01 q | 6.7 | 26.7 |
| 7' | 1.27 m | | 29.2 |
| 8' | 1.27 m | | 31.3 |
| 9' | 1.27 m | | 22.3 |
| 10' | 0.87 t | 7.2 | 13.1 |

$λ_{max}$ 252, 292 nm; $^1$H-NMR (METHANOL-D4, 600 MHz): δ ppm 5.88 (1H, s, 11-6), 5.36 (2H, m, H-4', H-5'), 3.04 (2H, t, J=7.2 Hz, $H_2$-2'), 2.37 (2H, q, J=7.3 Hz, $H_2$-3'), 2.01 (2H, q, $H_2$-6'), 1.89 (3H, s, 4-$CH_3$), 1.27 (6H, m, $H_2$-7', $H_2$-8', $H_2$-9'), 0.87 (3H, t, J=7.2 Hz, $H_2$-10'); $^{13}$C-NMR (METHANOL-D4, 150 MHz): δ ppm 205.3 (C-1'), 163.6 (C-3), 162.5 (C-5), 160.0 (C-2), 130.2 (C-5'), 128.4 (C-4'), 103.8 (C-1), 102.2 (C-4), 93.4 (C-6), 43.6 (C-2"), 31.3 (C-8'), 29.2 (C-7"), 26.7 (C-6"), 22.8 (C-3'), 22.3 (C-9"), 13.1 (C-10"), 6.0 (4-$CH_3$)

MALDI-TOF-MS m/z 291.5 [M-H]$^-$

Example 4 Tyrosinase Inhibition and Melanogenesis Inhibition with Compounds 1-3

The assay for tyrosinase activity was conducted in a procedure similar to that in Example 1 (3) using Compounds 1-3 as samples. In the tyrosinase activity assay, the final concentrations of each compound were adjusted to 100, 50, 25, and 12.5 mM and IC50 was calculated. Moreover, tests for melanogenesis inhibiting activity and for cytotoxicity were conducted in procedures similar to those in Example 2. The relative amount of extracellular melanin and the relative cell survival rate of skin melanocytes to which Compounds 1-3 were added were measured. The result of the tyrosinase activity assay is illustrated in Table 5 and the results of the measurements of the relative amount of extracellular melanin and the relative cell survival rate are illustrated in Table 6.

TABLE 5

| IC50 (μM) | Compound 1 | Compound 2 | Compound 3 | Kojic acid |
|---|---|---|---|---|
| Tyrosine | 125.34 | 480.51 | 83.98 | 64.58 |
| DOPA | 291.34 | 616.31 | 488.65 | 168.17 |

TABLE 6

| Sample | Concentration (μM) | Melanogenesis Activity (%) | Cell Viability (%) |
|---|---|---|---|
| Compound 1 | 200 | 13.6 | 64.9 |
| | 100 | 78.2 | 73.3 |

TABLE 6-continued

| Sample | Concentration (μM) | Melanogenesis Activity (%) | Cell Viability (%) |
|---|---|---|---|
| Compound 2 | 50 | 13.5 | 87.4 |
| | 25 | 99.0 | 95.0 |
| Compound 3 | 100 | 11.4 | 72.9 |
| | 75 | 9.7 | 92.5 |
| | 50 | 27.2 | 99.8 |
| | 25 | 106.6 | 94.3 |
| Arbutin | 730 | 32.7 | 107.6 |

The invention claimed is:

1. A method for inhibiting a tyrosinase in a human subject in need of inhibiting tyrosinase activity, comprising administering to the human subject an effective amount of *Syzygium polyanthum* or an extract therefrom.

2. A method for inhibiting melanogenesis in a human subject in need of inhibiting melanogenesis, comprising administering to the human subject an effective amount of *Syzygium polyanthum* or an extract therefrom.

3. A method for whitening skin in a human subject in need of skin whitening, comprising administering to the human subject an effective amount of *Syzygium polyanthum* or an extract therefrom.

* * * * *